US011406435B2

(12) United States Patent
Berger et al.

(10) Patent No.: US 11,406,435 B2
(45) Date of Patent: Aug. 9, 2022

(54) INSTRUMENTS AND INSTRUMENT KIT FOR LATARJET PROCEDURE AND ADAPTED METHOD

(71) Applicant: AZURMEDS INC., Chicago, IL (US)

(72) Inventors: Jean-Marie Berger, Eden Prairie, MN (US); Pierric Deransart, Saint martin d'Uriage (FR); Christopher R. Chuinard, Traverse City, MI (US); Thomas Bradley Edwards, Houston, TX (US); Grant E. Garrigues, Hinsdale, IL (US); Armodios M. Hatzidakis, Denver, CO (US); Gregory P. Nicholson, Western Spring, IL (US); Felix Buddy Savoie, New Orleans, LA (US)

(73) Assignee: AZURMEDS INC., Dallas, TX (US)

( * ) Notice: Subject to any disclaimer, the term of this patent is extended or adjusted under 35 U.S.C. 154(b) by 204 days.

(21) Appl. No.: 16/724,965

(22) Filed: Dec. 23, 2019

(65) Prior Publication Data
US 2020/0197030 A1 Jun. 25, 2020

Related U.S. Application Data

(60) Provisional application No. 62/783,780, filed on Dec. 21, 2018.

(51) Int. Cl.
*A61B 17/86* (2006.01)
*A61B 17/17* (2006.01)
(Continued)

(52) U.S. Cl.
CPC ........ *A61B 17/863* (2013.01); *A61B 17/1635* (2013.01); *A61B 17/1684* (2013.01); *A61B 17/1778* (2016.11); *A61B 17/68* (2013.01); *A61B 17/864* (2013.01); *A61B 17/8605* (2013.01); *A61B 17/8635* (2013.01); *A61B 17/8866* (2013.01); *A61B 34/10* (2016.02); *A61F 2/30749* (2013.01); *A61F 2/40* (2013.01);
(Continued)

(58) Field of Classification Search
CPC .............. A61B 34/10; A61B 2017/681; A61B 2017/567; A61B 2017/568; A61B 2017/564; A61B 2034/105; A61F 2/30749; A61F 2/40; A61F 2/4601; A61F 2/4644; A61F 2002/2835; A61F 2002/4627
USPC .......................................................... 606/96
See application file for complete search history.

(56) References Cited

U.S. PATENT DOCUMENTS

2014/0149095 A1* 5/2014 Davison ............... A61B 17/152
  703/7
2016/0374694 A1* 12/2016 Haberman ......... A61B 17/1635
  606/80

(Continued)

FOREIGN PATENT DOCUMENTS

FR 2996114 A1 4/2014

*Primary Examiner* — Marcela I. Shirsat
(74) *Attorney, Agent, or Firm* — Nixon & Vanderhye

(57) ABSTRACT

Disclosed is a positioning instrument that includes: two branches equipped at the proximal end thereof with an opposite jaw between which the graft is positioned, the two branches moving closer to one another by a translation movement; and a drill bush including a first hole and a second hole, separated by a distance and sized for the passage and guidance of a bone drill bit. Also disclosed are an instrument kit as well as a method for attaching a graft.

9 Claims, 14 Drawing Sheets

(51) Int. Cl.
*A61B 17/16* (2006.01)
*A61B 17/68* (2006.01)
*A61B 17/88* (2006.01)
*A61B 34/10* (2016.01)
*A61F 2/30* (2006.01)
*A61F 2/40* (2006.01)
*A61F 2/28* (2006.01)
*A61B 17/56* (2006.01)
*A61F 2/46* (2006.01)

(52) U.S. Cl.
CPC ... *A61B 2017/564* (2013.01); *A61B 2017/567* (2013.01); *A61B 2017/568* (2013.01); *A61B 2017/681* (2013.01); *A61B 2034/105* (2016.02); *A61F 2002/2835* (2013.01); *A61F 2002/4627* (2013.01)

(56) References Cited

U.S. PATENT DOCUMENTS

2017/0181759 A1* 6/2017 Bouduban .......... A61B 17/1778
2019/0070007 A1* 3/2019 Bettenga ............ A61B 17/0401

* cited by examiner

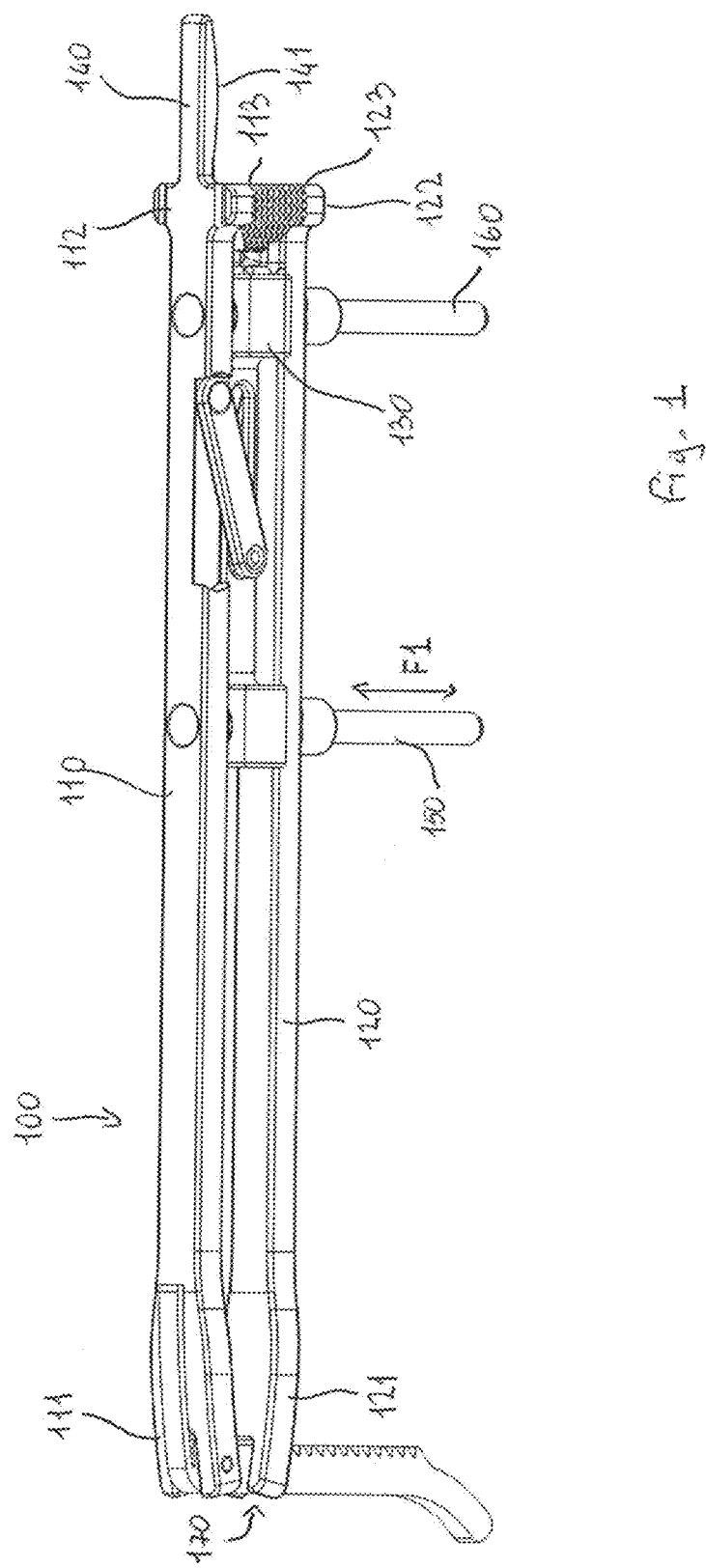

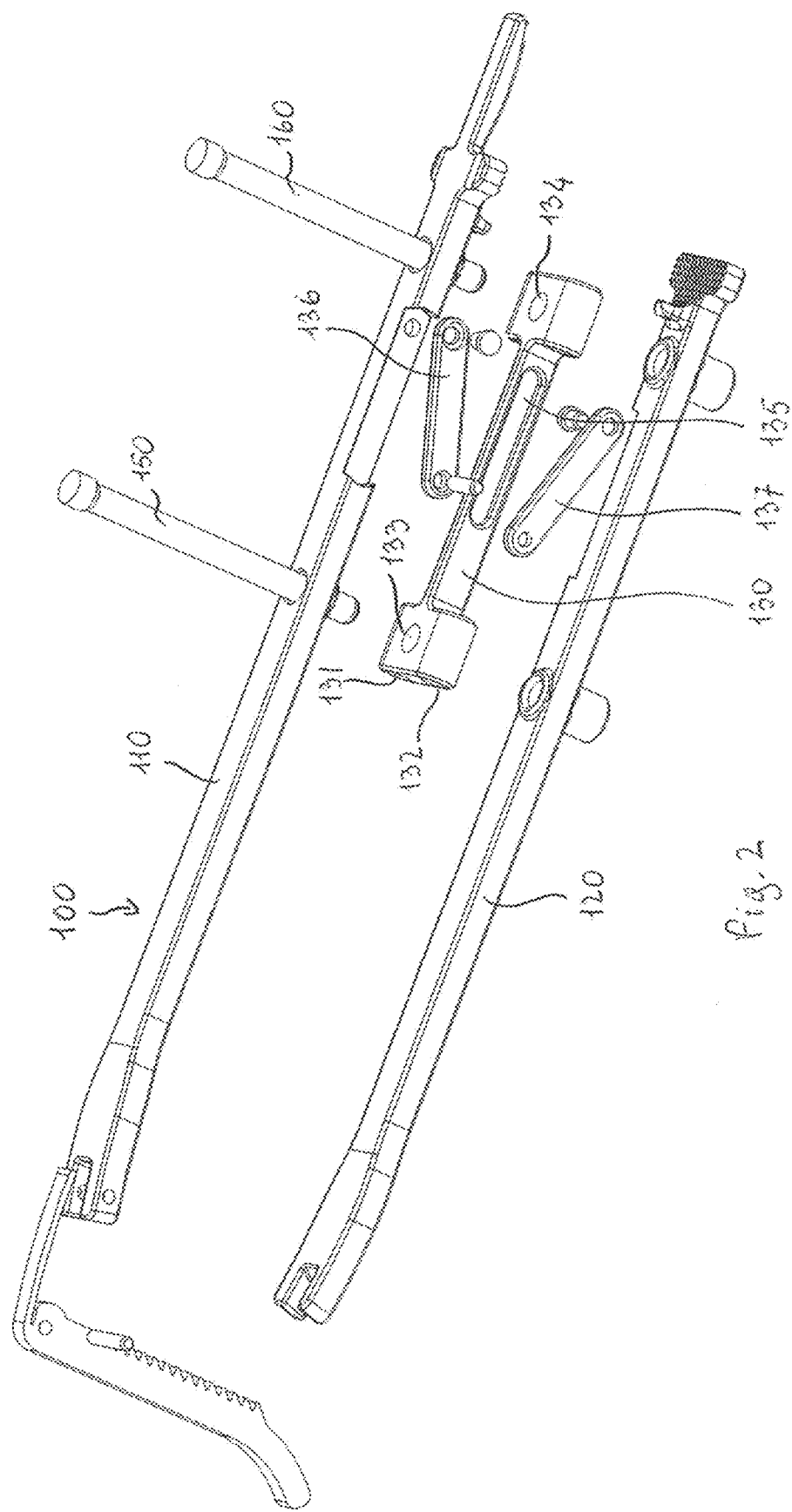

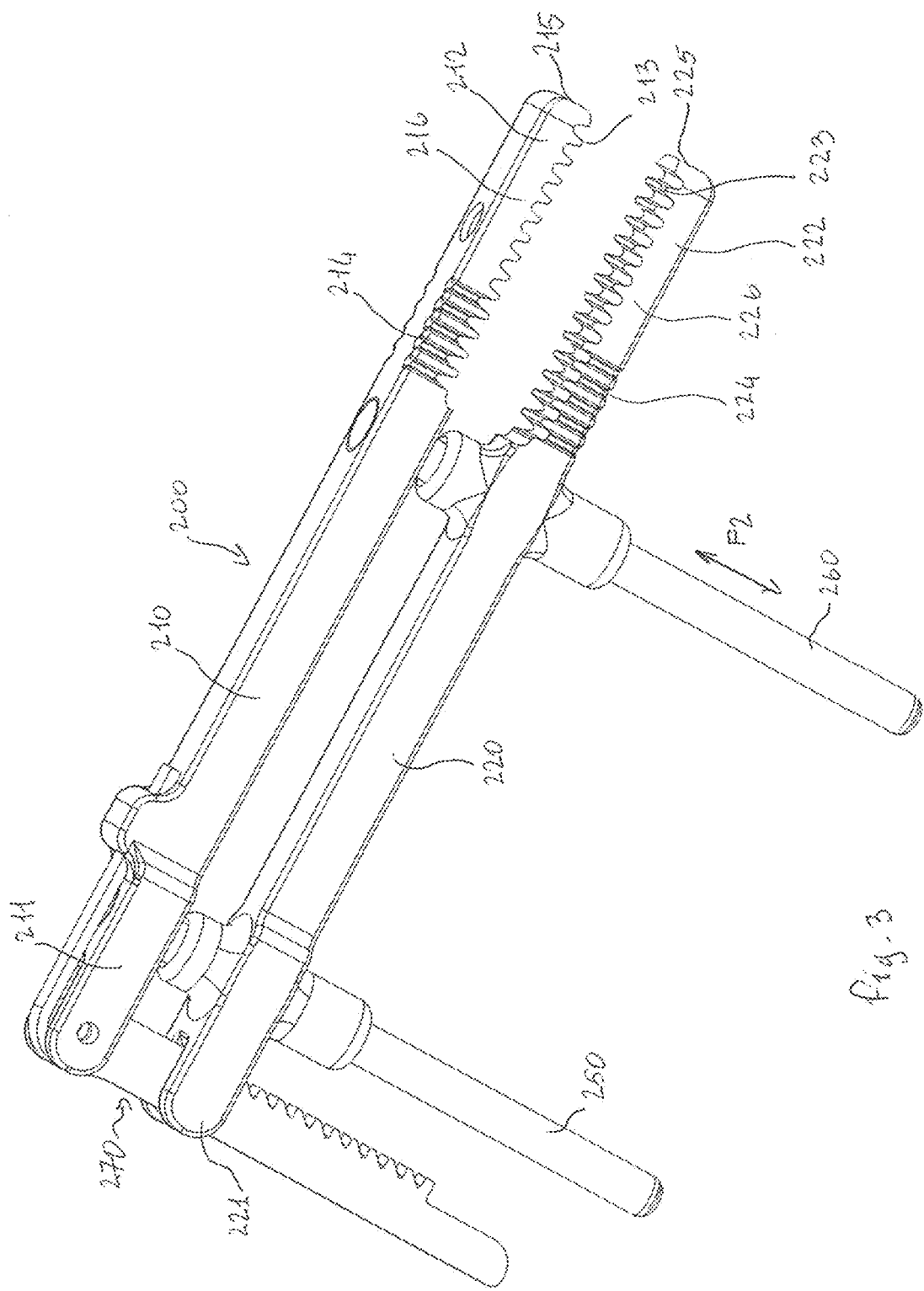

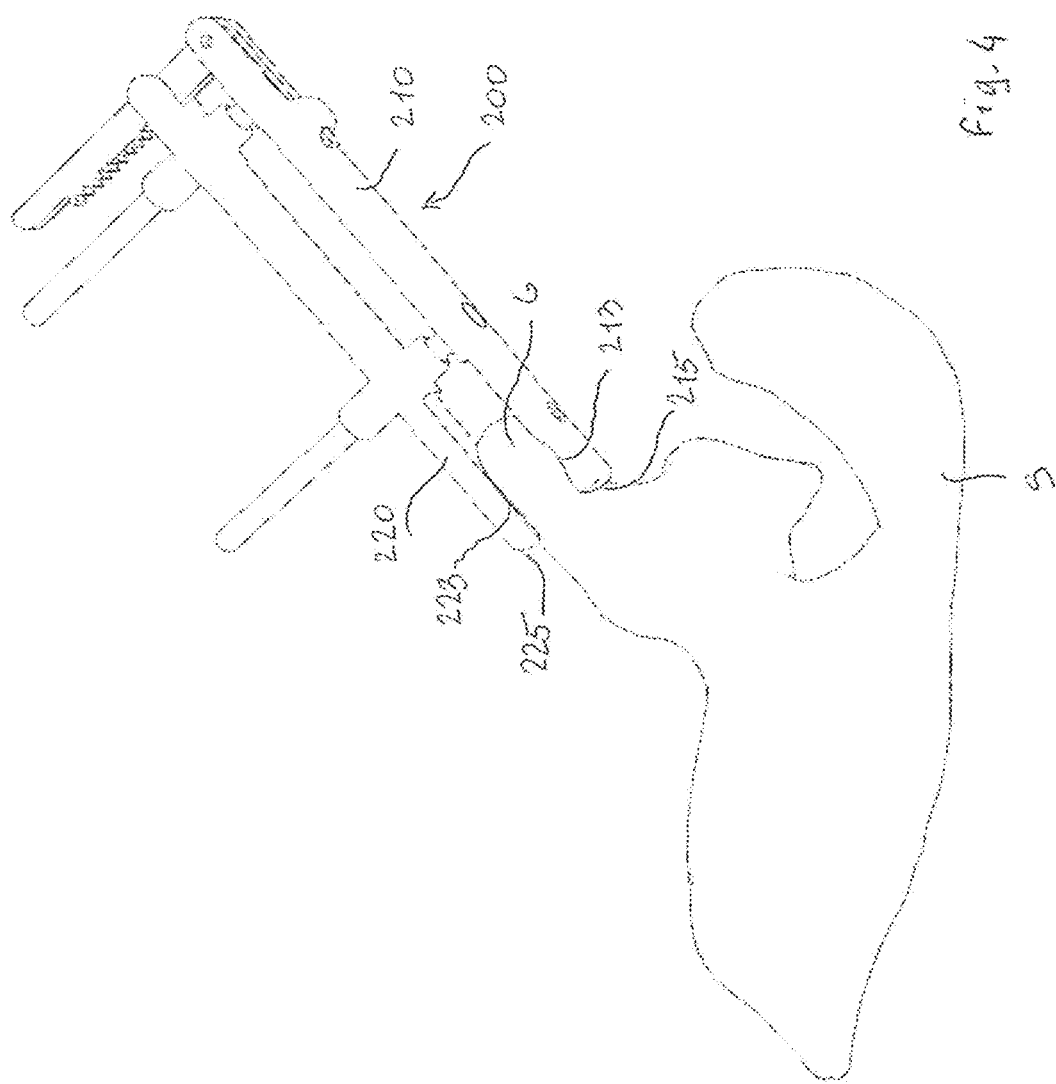

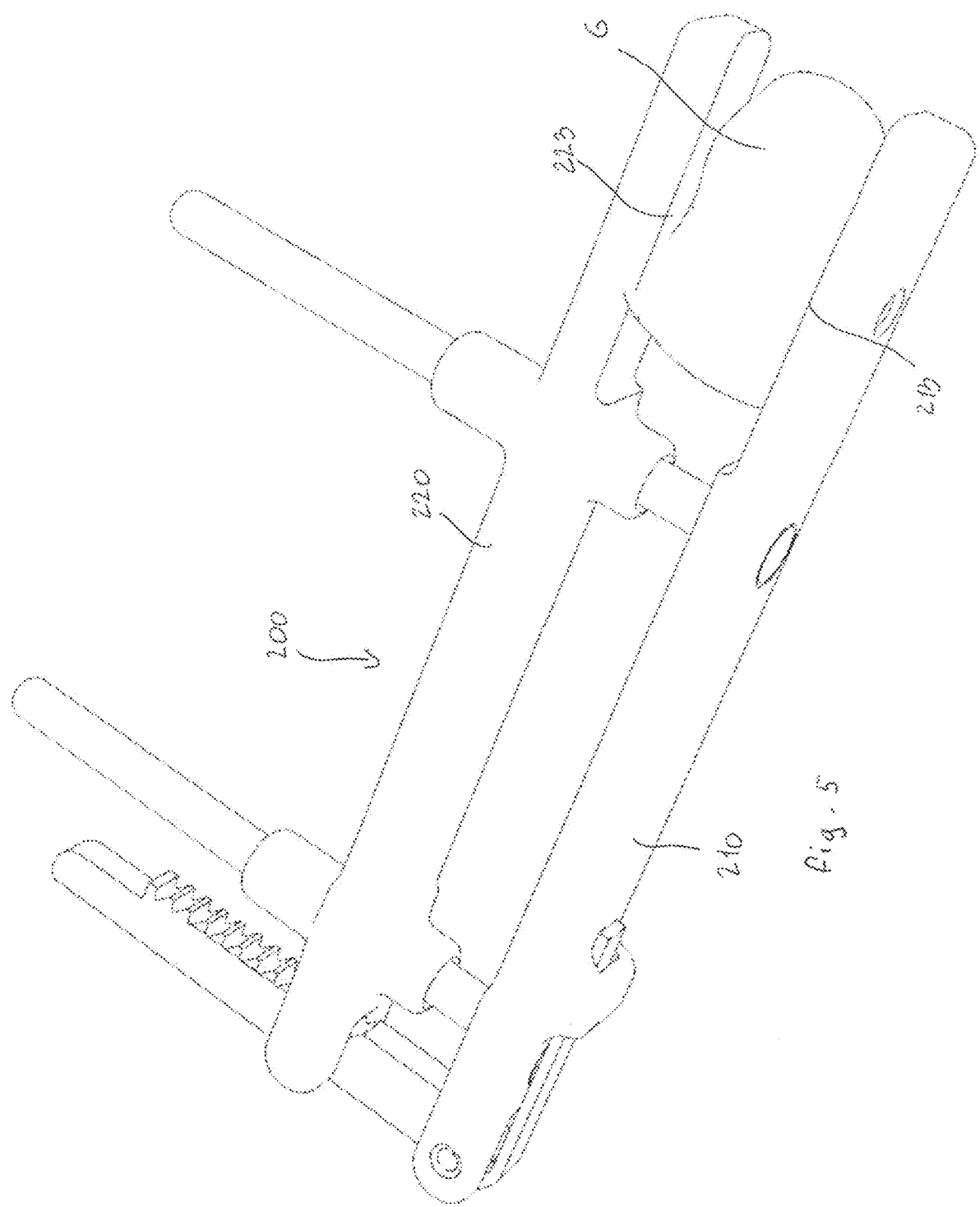

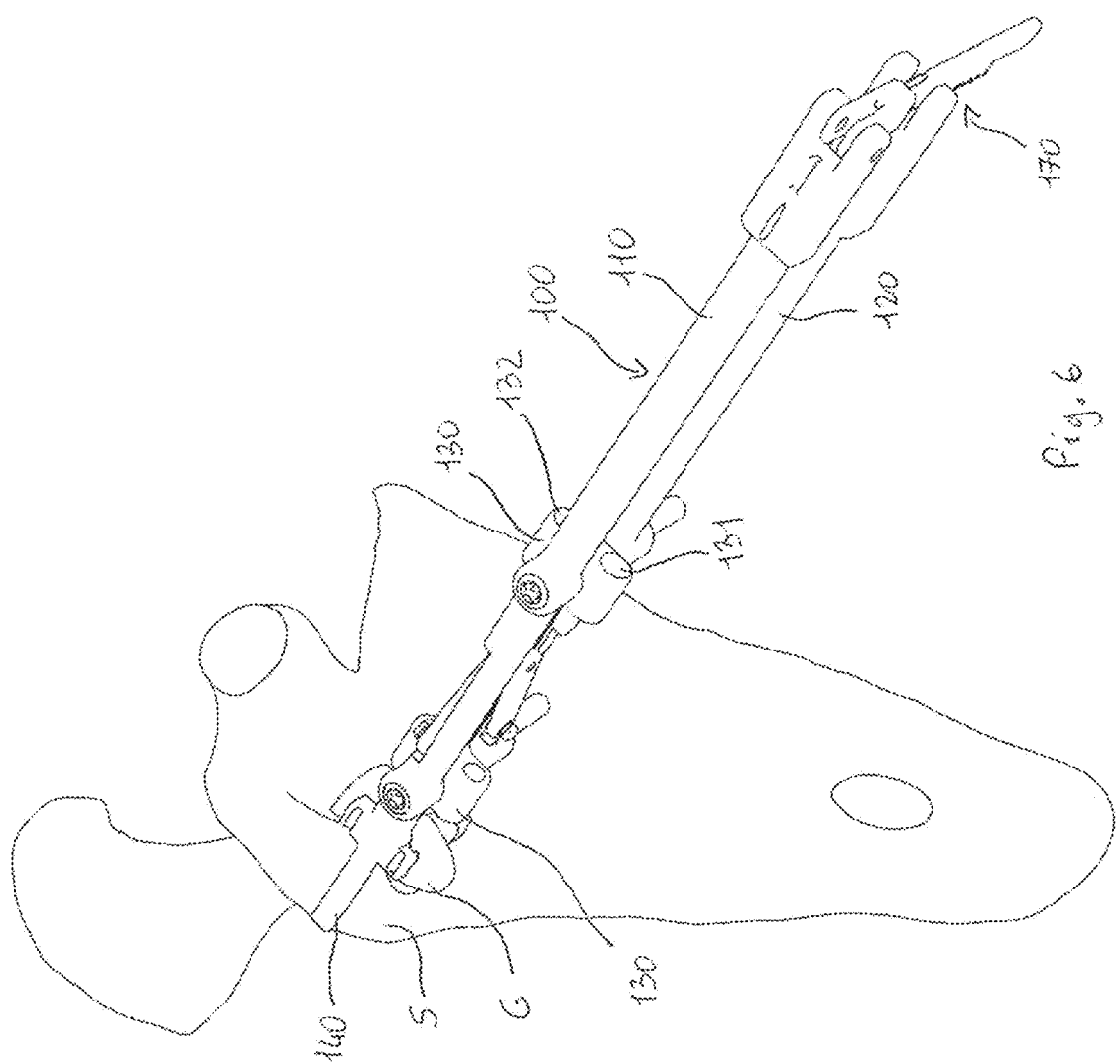

INSTRUMENTS AND INSTRUMENT KIT FOR LATARJET PROCEDURE AND ADAPTED METHOD

FIELD OF APPLICATION OF THE INVENTION

The invention relates to the field of surgical instruments involved in a so-called Latarjet surgical procedure and particularly to the adaptations of said instruments in order to optimize said procedure.

BRIEF DESCRIPTION OF THE PRIOR ART

The shoulder joint is known as the joint in the body with the greatest movement possibilities. Shoulder instability is a frequent condition which can be treated with surgical stabilization.

Among the known surgical stabilization procedures, there is known the so-called Latarjet procedure (from the name of the surgeon who was the first to describe it) consisting of performing a section of the coracoid (which is a natural excrescence or apophysis on the upper edge of the scapula) with the muscle which is inserted thereon (referred to as coraco-biceps). The subscapular muscle fibers are separated into two branches to open a median aperture in the longitudinal direction. The front of the scapula, exposed through the subscapularis, is refreshed. The sectioned portion of the coracoid is transferred through the subscapular muscle.

The coracoid section is positioned on the front of the scapula so as to have the lateral edge thereof continuous with the glenoid joint surface. It is then attached in this position by two bi-cortical screws, i.e. reaching the rear of the scapula.

This movement of a bone portion has two effects:
  it increases the diameter of the lower portion of the glenoid surface,
  the coraco-biceps tendon stabilizes the lower portion of the subscapularis by holding same pressed against the front of the scapula.

These two effects combined stabilize the humeral head by limiting the possibility of anterior luxation and/or dislocation.

The implementation of the different steps of this Latarjet procedure requires a plurality of instruments forming a dedicated instrument kit required for all or parts of the following operations:
  removal and preparation of the coracoid,
  movement of the graft,
  positioning and attachment of the graft on the scapula.

The positioning of the graft on the scapula must be very precise. A protrusion, even millimetric, of the graft with respect to the front edge of the glenoid surface may induce degradation of the humeral head with a medium or long-term risk of arthrosis. A recessed graft, even millimetric, from the front of the glenoid surface may induce luxation recurrences with a risk of extraction of the graft and deterioration of the bone lesions.

On this final operation, it is known that the drilling of the graft and the scapula are separate as described for example by the document FR2996114.

Similarly, the document US2016/0374694 describes a system and a method for coupling a graft with a bone. A graft preparation tool may be used to place one or a plurality of holes in a graft and an offset measurement tool may be used to determine the distance of the hole(s) from an edge of the graft to be aligned with a part of the bone. One or a plurality of complementary holes may then be created in the bone and screws applied through the holes to couple the graft with the bone.

This technique has a number of drawbacks, among these:
  it is complex and multiplies the steps requiring referencing the distances between the front edge of the coracoid and the axis of the bores thereof to be able to reproduce these distances when drilling the scapula with the risk of making an error during this referencing,
  the operating time is prolonged with the increase in the general anesthesia time, potential blood loss, infection risks,
  it has the non-negligible risk of poor alignment between the holes of the graft and the holes of the glenoid process,
  it has the non-negligible risk of an incorrect graft position,
  it renders the rectification of an incorrect position difficult or impossible.

BRIEF DESCRIPTION OF THE INVENTION

On that basis, the applicant conducted research aimed at optimizing the so-called Latarjet surgical procedure. This research resulted in the design and production of novel instrument kits intended to attach a bone graft onto a bone associated with novel methods for solving the problems of the prior art.

According to the invention, a first instrument kit for attaching a bone graft onto the scapula, is remarkable in that it comprises a positioning instrument which includes:
  two branches equipped at the proximal end thereof with an opposite jaw between which the graft is positioned, the two branches moving closer to one another by a translation movement, and
  a drill bush including a first hole and a second hole, separated by a distance and sized for the passage and guidance of a bone drill bit.

Approaching the jaws by means of a translation movement enables optimized accommodation and fastening of the bone graft with regard to those proposed by forceps with pivoting branches. Indeed, the rotation of the jaws, defines a different accommodation and fastening according to the size of the graft, which the design of the positioning instrument according to the invention avoids. Furthermore, the size of such forceps is reduced which enables much better use and much better visual monitoring by the operator.

This optimization facilitates carrying out simultaneous drilling of the bone graft and the scapula accommodating same.

According to a further particularly advantageous feature of the invention, one of the two branches is equipped with an extension preformed with a bearing surface against the glenoid joint surface in order to position the bone graft on the scapula.

By proposing referencing against the bone whereon the graft is to be fitted, the positioning means makes it possible to guide by means of said holes not only the graft drilling operation but also the guidance of the drilling operation of the bone receiving the graft.

Thus, the advantage of this technical feature is that of enabling graft and bone drilling operations to be carried out without handling the graft between the operations. A further advantage of this technical feature is that of making it possible to carry out graft and bone drilling operations at the same time. The operating time is then reduced.

Furthermore, it is then understood that the invention avoids any drawbacks associated with poor positioning of the holes created in the graft with those created in the bone receiving the graft since said bores are created without handling the graft or at the same time. The graft fitting precision is then enhanced.

According to a further particularly advantageous feature of the invention, said drill bush is positioned between said branches.

According to a further particularly advantageous feature of the invention, said holes of the drill bush have the same diameter between 2 mm and 5 mm.

According to a further particularly advantageous feature of the invention, said two branches are connected to one another by least one transversal connecting rod, the position of at least one branch with respect to this rod being adjustable, such that the spacing between the two branches is adjustable.

According to a further particularly advantageous feature of the invention, said two branches are connected to one another by at least two parallel transversal connecting rods so as to form a slide link allowing a first branch to move toward the other.

According to a further particularly advantageous feature of the invention, said drill bush is traversed by the two connecting rods so as to form a transversal axis slide link and is provided with a longitudinal slot wherein the pivoting shaft of the two ends of two tie rods of identical length moves, the first end of each tie rod being connected pivotally, respectively, to a different branch such that the axis of the holes of the drill bush is substantially in the median plane separating the two branches.

This feature makes it possible to systematically position the drill bush and the axes of the holes to be drilled defined thereby in the median plane defined by the two jaws. The axes of holes to be drilled are thus systematically correctly positioned.

According to a further particularly advantageous feature of the invention, said two branches include at the distal end thereof, a means for locking and tensioning the position of the branches receiving the bone graft between the jaws equipping the proximal end thereof.

It is understood that the use of the positioning instrument described above requires the supply of a bone graft. This bone graft may be a previously removed coracoid but may also be an outer quarter of the clavicle, a piece of crest of ileum, a bone from a bank, a bone substitute, etc.

In order to carry out this removal and/or prepare the graft, the applicant has devised an instrument kit also including a removal and/or preparation instrument.

According to a further particularly advantageous feature of the invention, the instrument kit further comprises an instrument for removing and/or preparing a graft to be removed or already removed which includes two branches equipped at the proximal end thereof with an opposite jaw between which the graft is positioned, said ends being preformed with a first planar surface to define a first cutting plane for the purposes of separating the graft from the bone to which it is attached, the two branches moving toward one another by a translation movement.

Accommodation and fastening are optimized by approaching the jaws in translation. Furthermore, the cutting required for removal is secured and facilitated since it is guided by the planar surface provided for this purpose.

According to a further particularly advantageous feature of the invention, said removal instrument comprises a second planar surface perpendicular to the first cutting plane to define a second cutting plane or indeed a referencing plane for the purposes of surfacing the graft portion coming into contact with the bone portion to receive said graft.

This feature is particularly advantageous in that it predetermines the positioning of a cutting plane with respect to the second which optimizes the positioning of the surfaces of the graft resulting from said cutting operations. Thus, the advantage of this feature is that of safeguarding and facilitating the baring of the surface of the graft coming into contact with the bone to receive said graft which promotes good contact between the surfaces of the graft and the host bone and promotes graft consolidation.

According to a further particularly advantageous feature of the invention, said two branches are connected to one another by two parallel transversal connecting rods, the position of at least one branch with respect to these rods being adjustable, such that the spacing between the two branches is adjustable.

According to a further particularly advantageous feature of the invention, said two branches include at the distal end thereof, a means for locking and tensioning the position of the branches receiving the bone graft between the jaws equipping the first end thereof.

According to the invention, a further instrument kit for attaching a bone graft to the scapula, is remarkable in that it is comprises a removal and/or preparation instrument described above and characterized in that it further includes:
  a central body traversed by the two connecting rods so as to form a transversal axis slide link and provided with a longitudinal slot wherein the pivoting shaft of the two ends of two tie rods of identical length moves, the first end of each tie rod being connected pivotally, respectively, to a different branch such that the central body is substantially in the median plane separating the two branches, and
  a drill bush, in the upper part of the central body, and including a first hole and a second hole, the axis of said holes being substantially parallel with the first planar surface of the branches and said holes separated by a distance between 4 mm and 6 mm and the first hole being sized for the passage of a pin and the second hole for the passage and guidance of a bone drill bit.

This arrangement facilitates the distal drilling of the graft before or after the removal thereof and before or after the baring of the surface of the graft called upon to be in contact with the host bone. The axis of the hole to be drilled is thus systematically correctly positioned substantially in the median plane of the graft.

According to a further particularly advantageous feature of the invention, said drill bush is free in translation relative to the central body. Thus, the advantage of this feature is that of safeguarding the positioning of the distal bore of the graft relative to the distal end of the graft. The axis of the hole to be drilled is thus systematically positioned at the correct distance from the distal end of the graft. It is understood that this alternative embodiment makes it possible to produce a first bore in the graft with the removal and/or preparation instrument.

It is then understood that a first hole must also be produced in the shoulder blade. In order to produce this hole, the applicant has devised an instrument kit also including a drilling instrument.

According to a further particularly advantageous feature of the invention, the instrument kit which comprises the removal and/or preparation instrument described above further comprises a positioning instrument which includes a handle and a drill bush including a single hole, sized for the passage and guidance of a bone drill bit, and including an extension preformed with a bearing surface against the glenoid joint surface.

This positioning instrument enables in a first phase the production of the lower hole in the scapula prior to positioning and attachment of the graft against the scapula by means of an attachment device inserted in the distal hole of the graft. This drilling instrument then makes it possible, in a second phase, to produce at the same time the second bore of the graft and of the scapula while still referencing on the glenoid joint surface by means of the preformed bearing surface extension. The graft fitting precision is then enhanced.

According to a further particularly advantageous feature of the invention, the same instrument sharing the same branches and the same jaws uses the positioning instrument and the removal and/or preparation instrument.

Such a design thus solves the problems of changing device to switch from the cutting operation to the drilling operation as well as those associated with moving the graft. Indeed, such a device allows the surgeon to cut, align and drill the coracoid and to attach the pre-prepared graft onto the scapula. It further makes it possible to position the graft on the scapula and use the holes of the graft as a positioning gauge for drilling means or to drill in a single operation, the graft and the scapula.

This then involves an "all-in-one" system but wherein the various functions may be used or not or then be used in a different sequence.

According to a further particularly advantageous feature of the invention, said jaws of at least one of the instruments are preformed to receive prefabricated grips selected from a plurality of grips offering a range of shapes and sizes adapted to the shapes and sizes of a coracoid or other graft.

According to a further particularly advantageous feature of the invention, said jaws at the proximal end of at least one of the instruments are preformed according to the shapes and sizes of a bone of the patient.

Thus, the jaw adopts a configuration adapted to the shape and sizes of the patient's coracoid or other graft.

According to a further particularly advantageous feature of the invention, the bearing surface against the glenoid joint surface of the positioning instrument is selected from a plurality of bearing surfaces offering a range of shapes and sizes adapted to shapes and sizes of a glenoid surface portion.

According to a further particularly advantageous feature of the invention, the bearing surface against the glenoid joint surface of the positioning instrument is preformed according to the shapes and sizes of the patient's bone.

Thus, the bearing surface of the extension of one of the two branches is preformed according to the shapes and sizes of the patient's glenoid joint surface.

According to a further particularly advantageous feature of the invention, the subassemblies coming into contact with the bones for fastening and/or referencing purposes (grips, bearing surface against the glenoid cavity, etc.) are attached detachably to the rest of the means (for securing or positioning) to which they belong.

According to a further particularly advantageous feature of the invention, the drill bush of at least one of the instruments is selected from a plurality of bushes offering guide holes adapted to the sizes of a coracoid or other graft.

According to a further particularly advantageous feature of the invention, at least one of the guide holes of a drill bush of at least one of the instruments described above is preformed to guide a bone drill bit adapted to the shape and sizes of the patient's bones.

Thus, the guidance of at least one of the bores to be produced adopts a configuration adapted to the shape and sizes of the patient's coracoid or other graft and/or of the patient's scapula.

According to an embodiment, the instrument kit is then broken down between common parts and parts belonging to a prefabricated or manufactured set according to the measurement and/or modeling of the patient's anatomy, bones and soft tissues, and attached at points to the common parts.

According to a further embodiment, at least one instrument of the instrument kit is designed and manufactured to adapt to a single patient's anatomy, bones and soft tissues.

An instrument kit according to the invention including all or some of the features described above provides the surgeons with guidance to safeguard the steps of the operations carried out. It is understood that the instrument kits according to the invention may be used for all or part of the Latarjet procedure. It is understood that the invention relates not only to the instrument kit but also to the constituent instrument(s) thereof.

These different features of an instrument kit according to the invention make it possible to envisage a plurality of methods of use, further subject matter of the invention.

A particularly advantageous feature of the method, which may be carried out by the instrument kit according to the invention is that it consists of positioning by means of a positioning instrument a bone graft on the scapula and of drilling said bone graft at the same time as the scapula with the aid of one or a plurality of drill bushes borne by the same positioning instrument.

Prior to the use or manufacture of an instrument kit and as an alternative or in addition to a configuration where a plurality of sets of prefabricated parts are to be selected according to the patient's anatomy, the method envisages a patient image acquisition operation (X-ray, scan, MRI, etc.).

Such a data acquisition phase is accompanied by a measurement phase on these data. These measurements result either in the determination of the positioning of one or a plurality of prefabricated instruments by replicating the measurements using references placed on the instrument(s), or the selection of all or some of one or a plurality of instruments from a set of prefabricated instruments.

According to a further embodiment, the data acquisition phase is accompanied by a three-dimensional reconstruction phase of the shoulder blade followed by a simulation phase of all or parts of the steps of operations to be carried out.

This simulation may help the practitioner when carrying out the actual operation, the invention further including the use of an augmented or mixed reality guidance means. Such a guidance means includes a screen positioned in the field of view of a user of the system and a data processing unit including an algorithm suitable for overlaying real visual elements, perceived directly or indirectly via a camera by the user, and virtual visual elements in a reference frame associated with said real visual elements.

The use of the guidance means consisting of providing in the form of virtual visual data the position and orientation data of at least one step of the operation, from the preparation of the graft and the positioning of the graft on the scapula.

According to a further embodiment, the data acquisition and three-dimensional shoulder blade reconstruction phases are accompanied by a modeling phase of all or parts of the instrumental system to be in contact with the patient's bones in question.

This modeling results either in the selection from a set of prefabricated parts or in the dedicated manufacture (by machining, molding, additive manufacturing, etc.) of at least one element from the reference surfaces coming into contact with the bone part to be fastened or whereon the device(s) are to bear and the guidance of the drilling to be carried out.

The method for using the instrument kit within the scope of the so-called Latarjet surgical procedure may then start.

According to a further particularly advantageous feature, the method comprises the following operations:
  providing a bone graft,
  providing a means for positioning a graft,—the positioning of an extension of the graft positioning means against the glenoid surface,
  producing one or a plurality of holes through the bone graft and the scapula,
  screwing screws passing through the graft in said holes for the purposes of attaching the graft to the scapula.

According to a further particularly advantageous feature, the method further comprises holding the graft in the graft positioning means, With regard to the field of application of the invention, it is obviously envisaged that the various subassemblies involved in the procedure are subject to a sterilization phase upstream from the surgical procedure per se. In the case of reusable instruments, this sterilization phase is carried out by the healthcare facility by means of a wet heat sterilization process According to a further particularly advantageous feature, the instruments are single-use and the sterilization phase is then carried out before providing the instrument kit to the healthcare facility by means of an ethylene oxide gas, gamma irradiation or electron beam sterilization process.

According to a further particularly advantageous feature, the method comprises prior to the selection or manufacture of all or part of the instruments, preoperative planning including the following operations:
  acquisition of imaging of the patient's shoulder (X-ray, scan, MRI, etc.);
  three-dimensional reconstruction of the shoulder blade;
  modeling of at least a part of the instrumental system to be in contact with the patient's bones in question, The basic concepts of the invention having been disclosed above in the more elementary form thereof, further details and features will emerge more clearly upon reading the following description and with reference to the appended drawings, giving by way of non-limiting example, of the embodiments of the invention.

BRIEF DESCRIPTION OF THE DRAWINGS

FIG. 1 is a schematic drawing of a perspective view of an embodiment of a positioning instrument according to the invention;

FIG. 2 is a schematic drawing of an exploded perspective view of the positioning instrument in FIG. 1;

FIG. 4 is a schematic drawing illustrating the removal of the coracoid by means of the instrument in FIG. 3;

FIG. 5 is a schematic drawing illustrating the instrument in FIG. 3 receiving the bone graft from the removal illustrated by FIG. 4 and positioned for baring of the surface required to be in contact with the scapula;

FIG. 6 is a schematic drawing of a perspective view illustrating the positioning of the bone graft on the scapula by means of the instrument in FIG. 1;

FIG. 9 is a schematic drawing of a perspective view of a further embodiment according to the invention of a removal and/or preparation instrument provided with a central drill bush;

DESCRIPTION OF PREFERRED EMBODIMENTS

Figure 7:
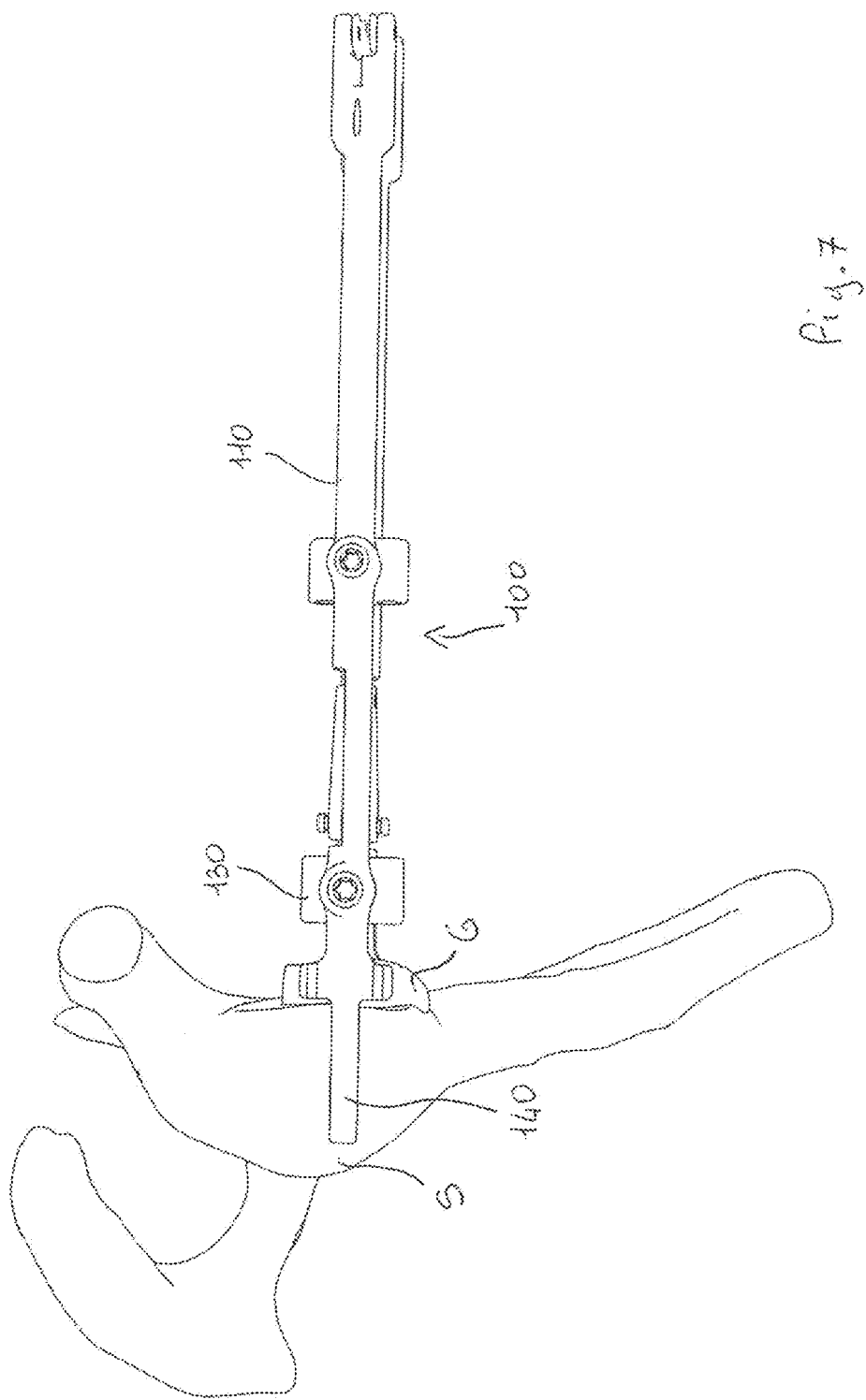
FIG. 7 is a schematic drawing of a front view illustrating the positioning of the bone graft on the scapula by means of the instrument in FIG. 1.

As illustrated by FIGS. 1 and 2, the positioning instrument referenced 100 as a whole includes two branches 110 and 120 arranged facing one another and having two ends 111 and 112 for the branch 110 and 121 and 122 for the branch 120.

Figure 8:
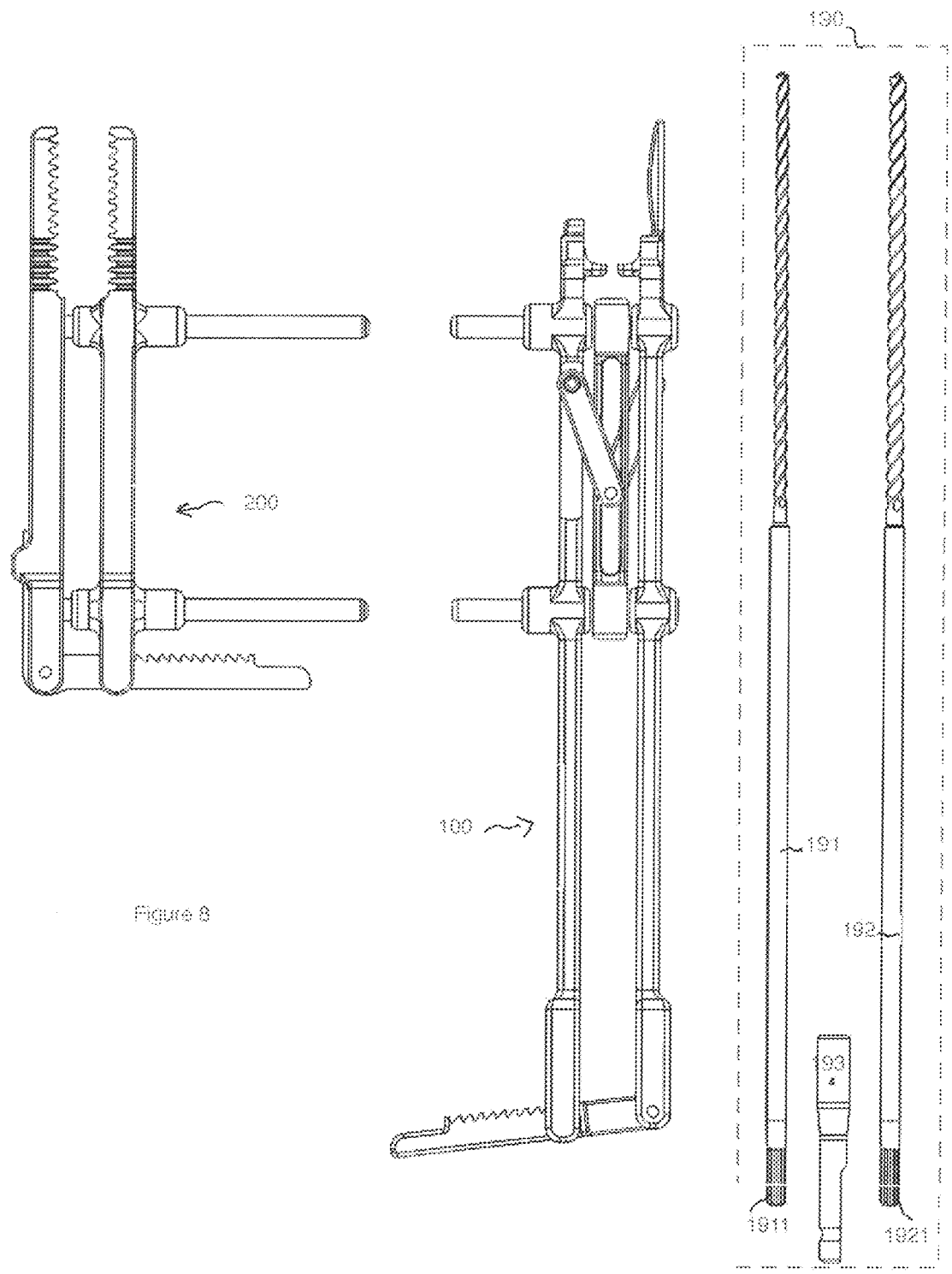
FIG. 8 is a schematic drawing illustrating a kit according to the invention including the positioning instrument in FIG. 1 and the removal and/or preparation instrument in FIG. 3.

The proximal ends 112 and 122 arranged facing one another are each preformed with a jaw 113 and 123 between which the graft G is positioned (see FIGS. 7 and 8). This instrument 100 is designed such that the two branches 110 and 120 move toward or away from one another by a translation movement represented by the double arrow F1.

The positioning instrument 100 further comprises a drill bush 130 including a first hole 131 and a second hole 132 substantially parallel and separated by a distance between 8 mm and 16 mm and sized for the passage and guidance of bone drill bits.

The branch 110 extends beyond the performed jaw portion 113 with an extension 140 preformed with a bearing surface 141 against the glenoid surface so as to position the bone graft G on the scapula S prior to the simultaneous drilling thereof with the scapula.

In order to use the slide allowing the translation movement along the double arrow F1, the instrument 100 comprises two parallel transversal connecting rods 150 and 160. A first end of said rods 150 and 160 is attached to a first branch 110 and the second branch 120 is preformed with guide sleeves to enable the sliding thereof along the rods 150 and 160 and thus separate or approach the jaws 113 and 123.

As illustrated, said drill bush 130 is positioned between said branches 110 and 120 such that the axes of the holes 131 and 132 are arranged respectively on either side of the plane defined by the axes of the parallel rods 150 and 160.

So as not to form an obstacle to this sliding but also so as to enable the correct systematic positioning of the drill bush 130 the latter is drilled with two transversal holes 133 and 134 to be traversed by said two connecting rods 150 and 160. The drill bush 130 is therefore also in a slide link along said rods.

There is further provided a longitudinal slot 135 wherein the shaft 138 connected rigidly to one of the two ends and pivotally to the other second ends of two tie rods 136 and 137, of identical length, moves, the first end being pivotally connected, respectively, to a different branch 110 or 120. These hinged tie rods 136 and 137 carry out the positioning of the drill bush 130 such that the axes of the holes 131 and 132 are the median plane separating the two branches 110 and 120 and therefore the two jaws 113 and 123 regardless of the spacing of the branches 110 and 120.

According to the embodiment illustrated, the approach or separation of the two branches 110 and 120 is carried out manually.

According to a further embodiment not illustrated, the movement may be carried out by means of a third rod including two threaded portions each engaged in a different branch.

Once the graft has been received between the jaws 113 and 123, it is necessary to lock the position. To do this, said two branches 110 and 120 include at the distal end 111 and 121 thereof, a locking and tensioning means connecting same. According to the preferred and non-limiting embodiment illustrated, this consists of a rack lock 170.

According to a further embodiment not illustrated, the locking may be carried out by means of a wheel engaging with a threaded portion of one of the transversal rods.

Figure 3:
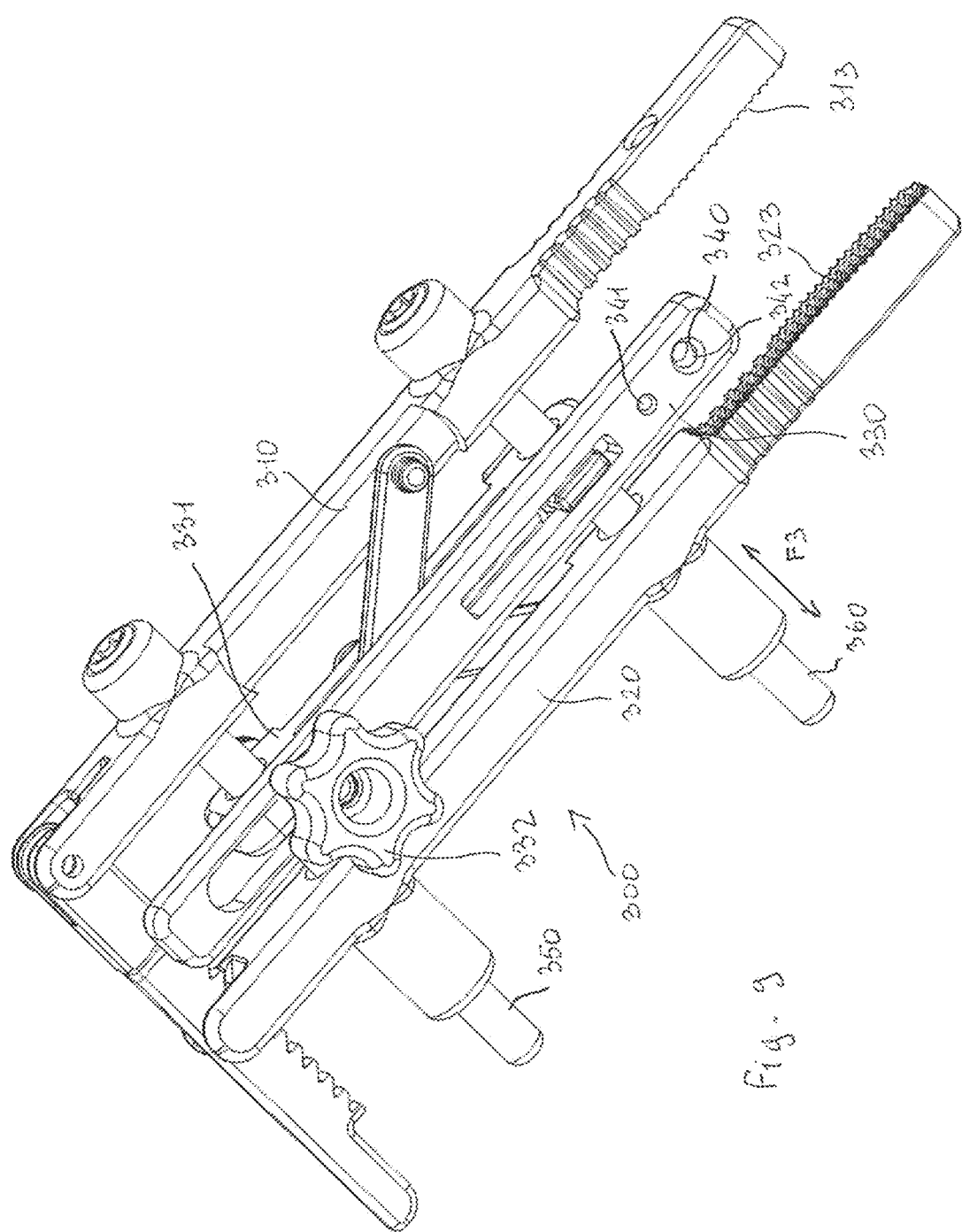
FIG. 3 is a schematic drawing of a perspective view of a removal and/or preparation instrument according to the invention.

As illustrated by FIG. 3, the instrument for removing and preparing a graft referenced 200 as a whole takes on the same configuration as the positioning instrument i.e. it forms forceps wherein the branches move toward or away from each other according to a translation movement along the double arrow F2.

To do this, the instrument 200 includes two branches 210 and 220 arranged facing one another and having two ends 211 and 212 for the branch 210 and 221 and 222 for the branch 220.

The proximal ends 212 and 222 arranged facing one another are each preformed with a jaw 213 and 223 between which the graft G (to be removed or removed) is positioned (see FIGS. 5 and 6).

The ends 212 and 222 arranged facing one another are further each preformed on at least one different face from that supporting the jaws 213 and 223 but in the vicinity thereof, with notches 214 and 224. These notches 214 and 224 serve as positioning marker of the graft G between the jaws 213 and 223.

Said proximal ends 212 and 222 are further preformed:
  with a first planar surface 215 and 225 to define a first cutting plane for the purposes of separating the graft from the bone to which it is attached.
  a second planar surface 216 and 226 to define a second cutting plane or indeed a referencing plane perpendicular to the first cutting plane for the purposes of surfacing the graft portion coming into contact with the bone portion to receive said graft.

To carry out the translation along the double arrow F2, the instrument 200 comprises two parallel transversal connecting rods 250 and 260. A first end of said rods 250 and 260 is attached to a first branch 210 and the second branch 220 is preformed with guide sleeves to enable the sliding thereof along the rods 250 and 260 and thus separate or approach the jaws 213 and 223.

Once the graft has been received between the jaws 213 and 223, it is necessary to lock the position. To do this, said two branches 210 and 220 include at the distal end 211 and 221 thereof, a locking and tensioning means connecting same. According to the preferred but non-limiting embodiment illustrated, this consists of a rack lock 270.

FIGS. 4, 5, 6 and 7 illustrate a plurality of steps of a so-called Latarjet procedure carried out by the instruments 100 and 200 described above. As explained above, one benefit of the novel features of the instruments is that of carrying out a method which is remarkable in that it consists of positioning by means of the positioning instrument 100 a bone graft G on the scapula S and drilling said bone graft G at the same time as the scapula S with the aid of the drill bushes 130 borne by the same positioning instrument 100. FIGS. 4 to 7 illustrate such a method with beforehand the removal of the coracoid in order to have a bone graft G to be attached as illustrated in FIGS. 4 and 5. The jaws 213 and 223 take the coracoid or bone graft G in the length thereof to fasten same in the width thereof.

Once the removal instrument 200 is in place as illustrated in FIG. 4, the practitioner may use the surfaces 215 and 225 as a cutting plane.

FIG. 5 illustrates the position of coracoid or bone graft G during resurfacing. To do this, the coracoid is turned in the forceps. In other words, after the resection of the coracoid, the removal instrument is unfastened and the graft removed from the coracoid is turned therein (the bottom face becomes the top face and the resected face is inserted first into the jaws) to have access more readily to the surface to be freshened.

As illustrated by FIGS. 6 and 7, for the positioning means 100, the coracoid or bone graft G is taken in the thickness thereof to be fastened in the width thereof. Once the graft G has been locked between the jaws 113 and 123, the positioning means is positioned bearing against the scapula using the extension 140 thereof. The simultaneous drilling of the graft G and the scapula S can then start leaving for each bore the bit used in place. After producing two bores, the positioning instrument 100 is removed while leaving the drill bits in place. Successively, the drill bits are removed and replaced by compression screws or a further attachment means.

FIG. 8 illustrates an instrument kit according to the invention which comprises the positioning instrument referenced 100, the instrument for removing and preparing a graft referenced 200 and a drilling kit 190. The drilling kit 190 includes at least two drill bits 191 and 192 suitable for being inserted into the holes 131 and 132 of the drill bush 130 and provided at the distal end 1911 and 1921 thereof with a means for engaging with a drive tool 193 such that the engagement means does not impede the sliding of the drill bits 191 and 192 in the holes 131 and 132.

FIG. 9 illustrates a different embodiment of the instrument for removing and preparing the coracoid or a graft G. The instrument 300 with the branches 310 and 320 and the jaws 313 and 323 uses the removal and/or preparation instrument. As a whole, it adopts the same configuration as the positioning instrument 100 i.e. it forms forceps wherein the branches move closer or apart according to a translation movement along the double arrow F3.

The instrument 300 further includes a central body 330 traversed by the two connecting rods 350 and 360 so as to form a transversal axis slide link. Similarly to the drill bush 130, the central body 330 is provided with a longitudinal slot wherein the shaft of the two ends of two tie rods of identical length moves, the first end of each tie rods being connected pivotally, respectively, to a different branch such that the central body is substantially in the median plane separating the two branches.

Said central body 330 further includes a means for guidance in translation 331 and a fastening means 332 both capable of engaging with a drill bush 340 including a first hole 341 sized for the passage and guidance of a pin and a second hole 342 sized for the passage and guidance of bone drill bits. The drill bush 340 is free to translate along an axis represented by the double arrow F4 and perpendicular to the double arrow F3. The fastening means 332 is suitable for locking the drill bush in a desired position relative to the graft G.

These features make it possible to position systematically the central body 330, the bush 340 and the guide axis of the holes 341 and 342 in the median plane defined by the two jaws. A pin inserted into the hole 341 makes it possible to identify the distal end of the graft while being flush therewith. The axis of the hole 342 is thus systematically correctly positioned. The removal and preparation instrument 300 makes it possible to carry out the distal drilling of the graft with the removal and/or preparation instrument.

Figure 10:
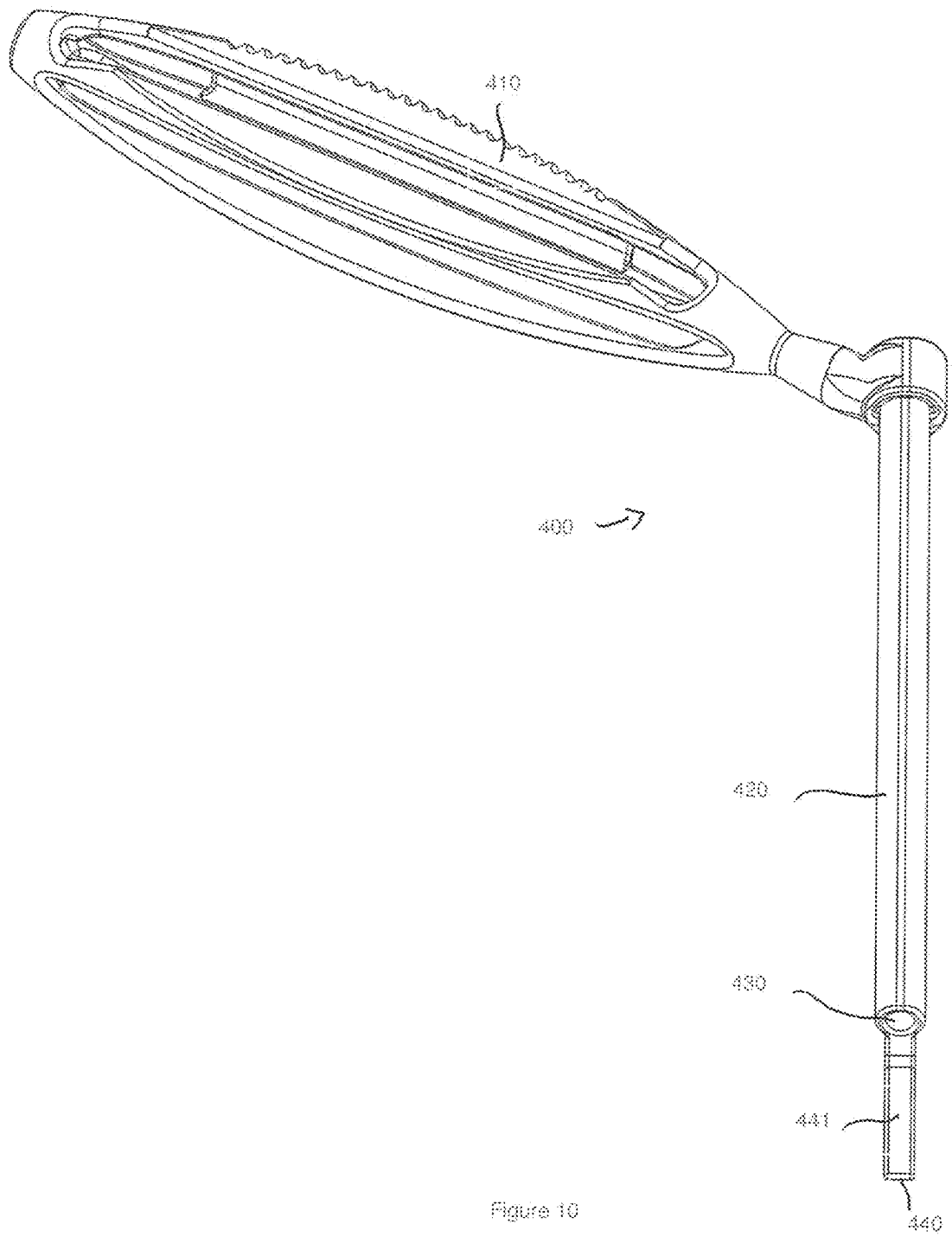
FIG. 10 is a schematic drawing of a perspective view of a further embodiment of a positioning instrument provided with a drill bush and a bearing surface.

FIG. 10 illustrates a different embodiment of the instrument for positioning the graft G on the scapula S. The positioning instrument referenced 400 as a whole includes a handle 410 and a drill bush 420 including a hole 430 sized for the passage and guidance of bone drill bits.

The drill bush 420 extends beyond the proximal end of the hole 430 with an extension 440 preformed with a bearing surface 441 against the glenoid surface so as, in a first phase, to position the drill bush on the scapula S then, in a second phase, to position the bone graft G on the scapula S.

According to an embodiment not illustrated, the drill bush 420 may be inserted into the handle 410 in two mirror positions relative to one another suitable for being adapted to the laterality of the operated shoulder.

Figure 11:
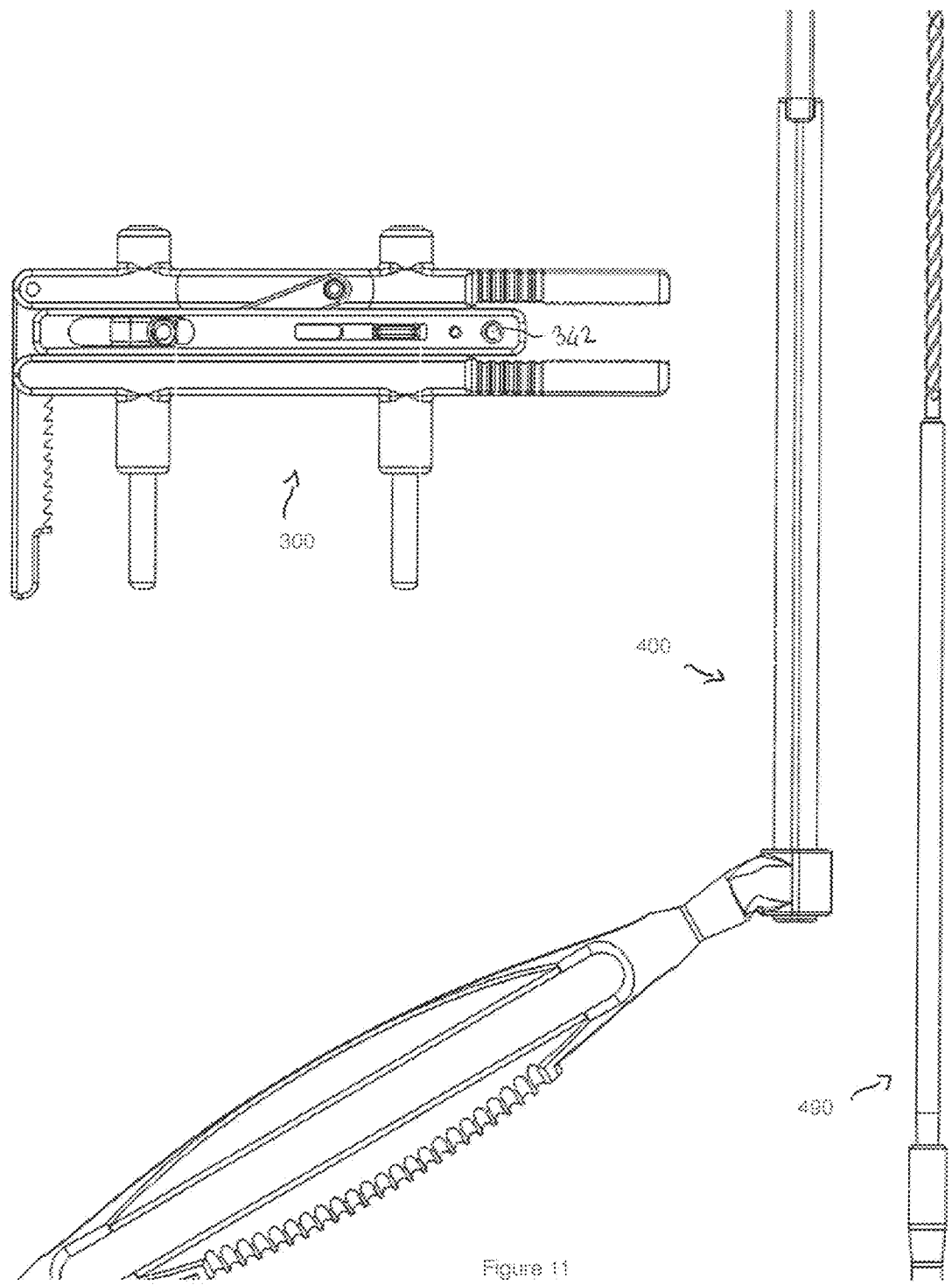
FIG. 11 is a schematic drawing illustrating a kit according to the invention including the positioning instrument in FIG. 10 and the removal and/or preparation instrument in FIG. 9.

FIG. 11 illustrates an instrument kit according to the invention which comprises the instrument for removing and preparing a graft referenced 300, the positioning instrument referenced 400 and at least one drill bit 490 suitable for being inserted into the holes 342 and 430 of the drill bushes 340 and 420.

Figure 12:
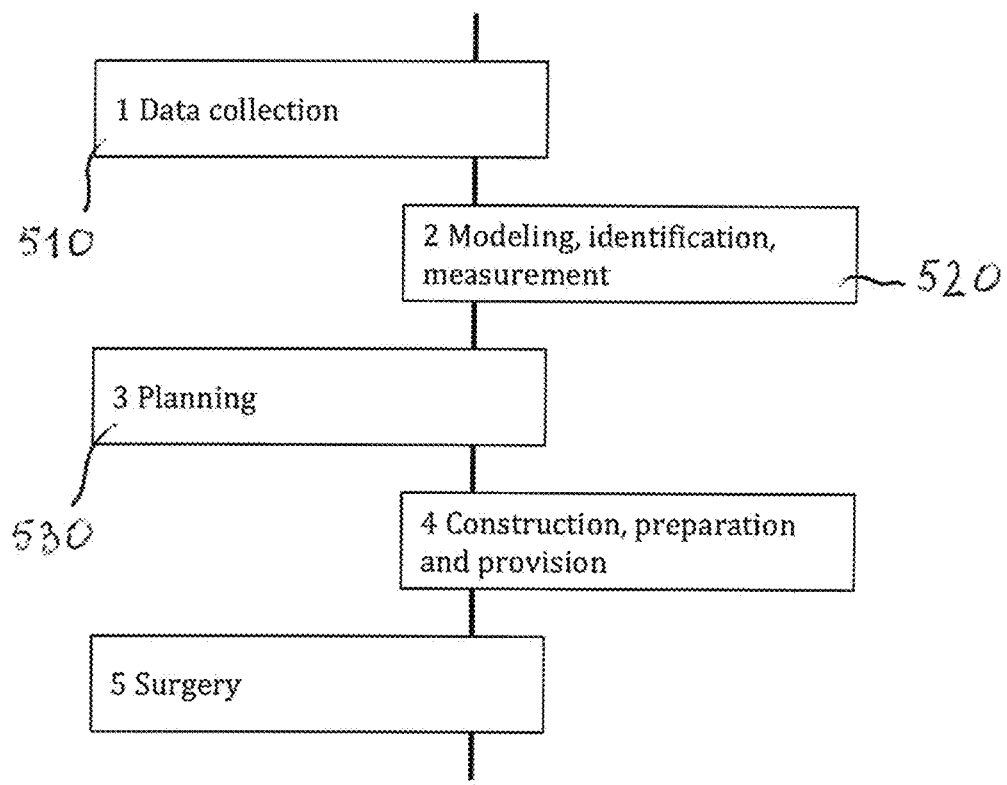
FIG. 12 is a diagram of the main phases of the process leading to the creation of an instrumental system and/or an attachment method according to the invention specific to a patient.

FIG. 12 illustrates the method comprising prior to the selection or manufacture of all or part of the instruments, preoperative planning.

Prior to the surgical procedure, during the data collection phase 510, the preoperative imaging of the patient to be operated on is acquired in various ways. By way of example, X-rays and/or sonographies and/or CT scan and/or MRI images of the shoulder are used.

Based on the preoperative imaging of the patient to be operated on, during a modeling and identification phase 520, at least one segmentation and processing algorithm makes it possible to model the patient's joint and identify at least one anatomical structure. This phase may include the measurement of at least one specific characteristic of the patient's joint.

During the planning phase 530, the surgeon carries out preoperative planning by means of a computer interface suitable for viewing the modeling of the joint and carrying out at least one of the following operations: sizing the graft, positioning the graft on the host bone and positioning and selecting the devices for attaching the graft onto the host bone.

This method may further include the formation, manufacture and provision for the surgical procedure of a patient-specific instrument kit produced based on the data previously collected and, in particularly, the planning output data.

Figure 13:
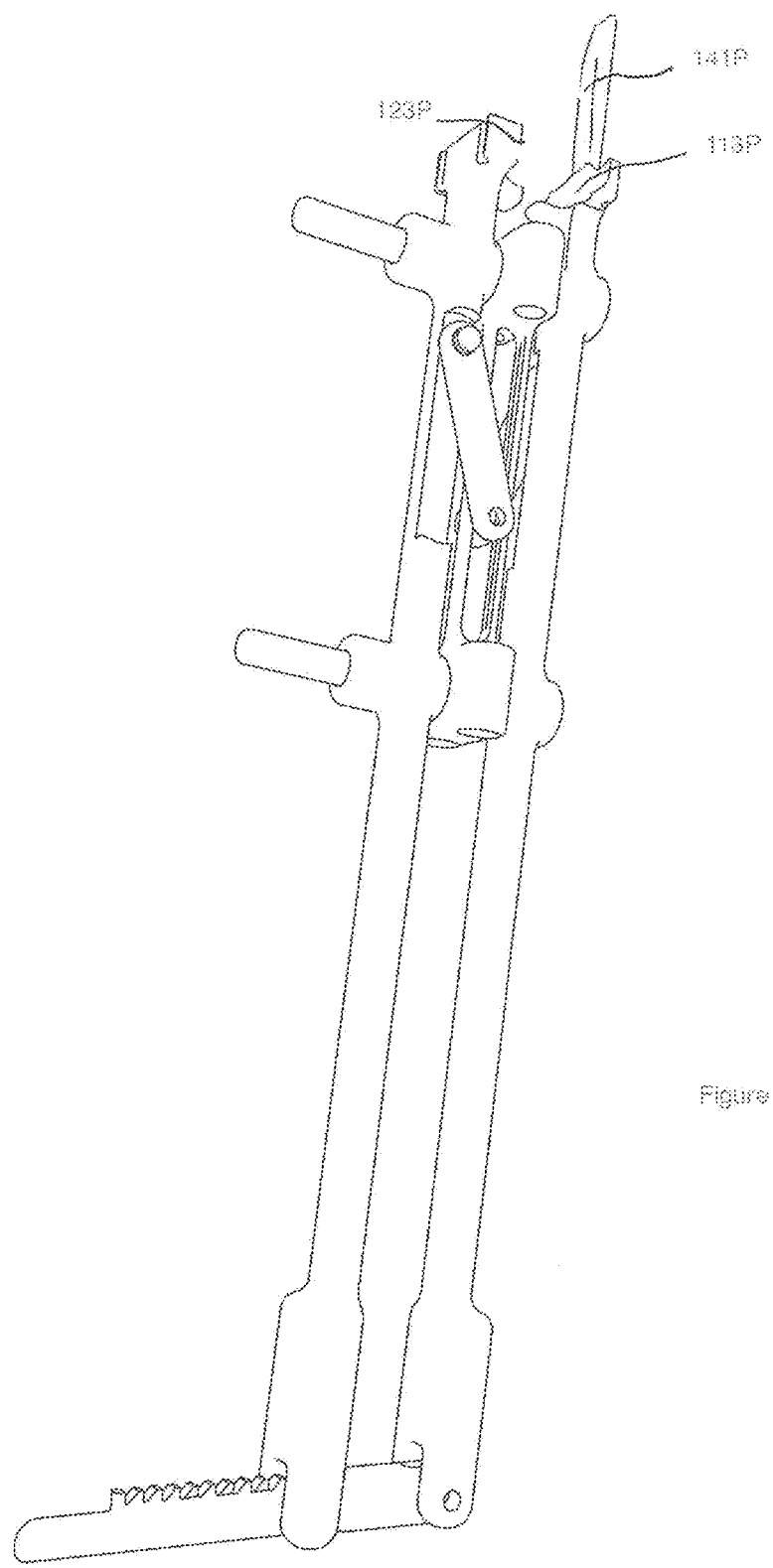
FIG. 13 is a schematic drawing of a perspective view of an embodiment of a positioning instrument with jaws and a bearing surface formed according to the patient's bone according to the invention.

FIG. 13 illustrates a positioning instrument of FIG. 1 wherein the jaws 113P and 123P and the bearing surface 141P are preformed according to preoperative planning as described above. Such a structure of the jaws has the advantage of ensuring unique positioning of the graft between the jaws and relative to the drill bush. Furthermore, the structure of the bearing surface on the glenoid surface ensures unique positioning of the graft on the scapula.

Figure 14:
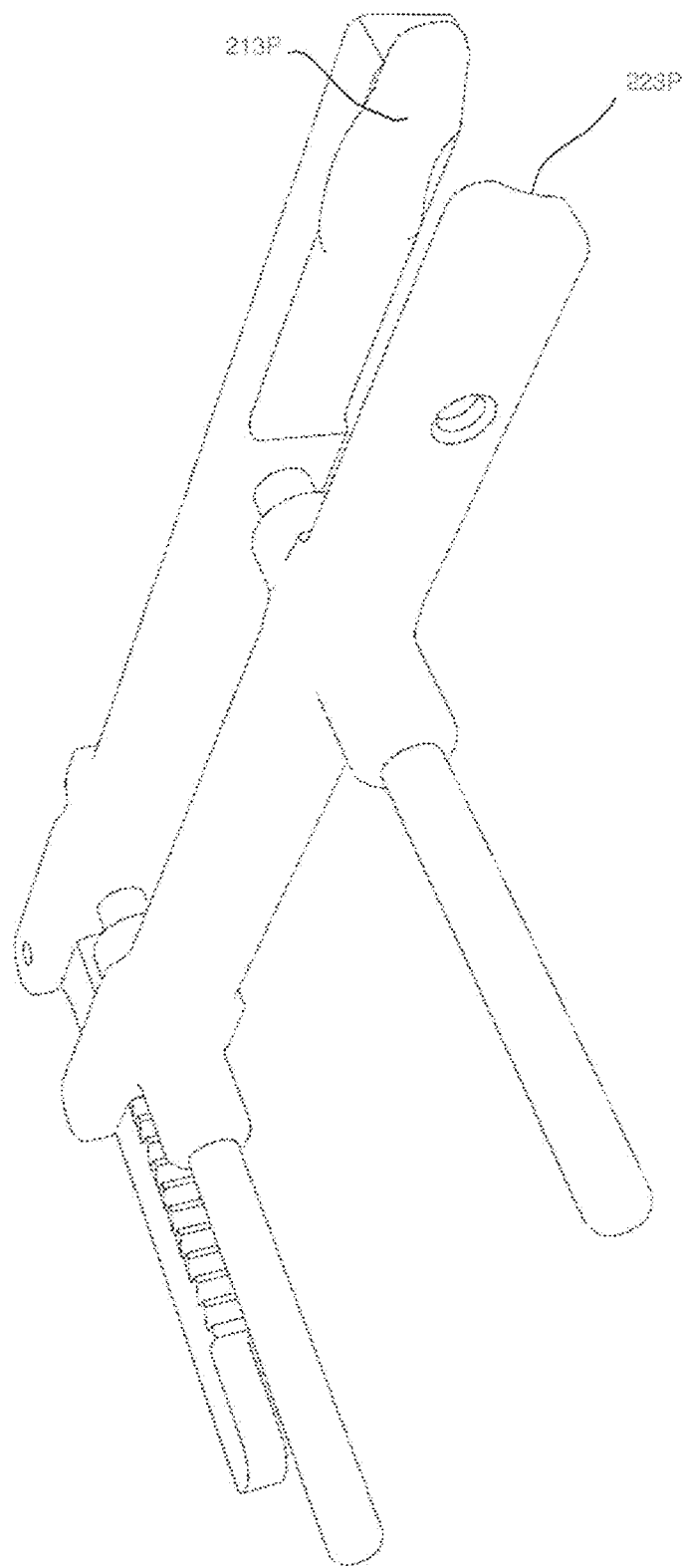
FIG. 14 is a schematic drawing of a perspective view of an embodiment of a removal and/or preparation instrument with jaws formed according to the patient's bone according to the invention.

FIG. 14 illustrates an instrument for removing and preparing a graft of FIG. 3 wherein the jaws 213P and 223P are preformed according to preoperative planning as described above. Such a structure of the jaws has the advantage of ensuring unique positioning of the graft between the jaws.

It is understood that the instrumental system and the adapted methods described and represented above have been described and represented with a view to disclosure rather than limitation. Obviously, various adaptations, modifications and improvements may be made to the above examples, without leaving the scope of the invention.

The invention claimed is:

1. A method for attaching a bone graft to a scapula, the method comprising:
   providing a bone graft free of any holes;
   producing a first hole at the same time in the bone graft and in the scapula;
   producing a second hole at the same time through the bone graft and the scapula; and
   screwing screws passing through the graft in said holes to attach the bone graft to the scapula.

2. The method for attaching the bone graft to the scapula according to claim 1, further comprising providing a clamp configured to remove and prepare the bone graft free of any holes.

3. The method for attaching the bone graft to the scapula according to claim 1, further comprising providing a graft positioning clamp configured to position against the scapula and bone graft free of any holes.

4. The method for attaching the bone graft to the scapula according to claim 3, further comprising positioning an extension of the graft positioning clamp against the glenoid surface.

5. The method for attaching the bone graft to the scapula according to claim 4, further comprising drilling the first hole at the same time in said bone graft and in the scapula with the aid of a drill bush borne by the graft positioning clamp.

6. The method for attaching the bone graft to the scapula according to claim 1, further comprising:
   positioning the first hole at the same time in the bone graft and in the scapula by a drill bush borne by a graft positioning instrument; and
   positioning and drilling the second hole in the bone graft at the same time as the scapula with the aid of the drill bush borne by the graft positioning instrument.

7. The method for attaching the bone graft to the scapula according to claim 1, further comprising, based on preoperative planning, selecting a graft positioning instrument from a plurality of prefabricated instruments including a variety of sizes and shapes of one or more of: (i) graft-holding jaws, and (ii) glenoid extension surfaces.

8. The method for attaching the bone graft to the scapula according to claim 1, further comprising, prior to using an instrument kit:

acquiring imaging of a shoulder of the patient;
three-dimensionally reconstructing the shoulder blade;
modeling at least a part of a clamp configured to remove and prepare the bone graft or a graft positioning instrument; and
manufacturing at least a part of the clamp or the graft positioning instrument.

9. The method for attaching the bone graft to the scapula according to claim 1, further comprising, using, based on preoperative planning, an intraoperative guidance solution including providing, by virtual visual elements overlaid on real visual elements, position and orientation data of at least one step of an operation from cutting to separate the bone graft from a bone to which the bone graft is attached, baring the surface of the bone graft to come in contact with the scapula, and positioning the bone graft on the scapula and drilling the graft and the scapula.

* * * * *